(12) United States Patent
Lund et al.

(10) Patent No.: US 10,718,365 B2
(45) Date of Patent: Jul. 21, 2020

(54) MOUNTING CLAMP DEVICE

(71) Applicant: Dragerwerk AG & Co., KGAA, Lubeck (DE)

(72) Inventors: Peter Andrew Lund, Nashua, NH (US); Ashleigh C. Collins, Derry, NH (US)

(73) Assignee: DRÄGERWERK AG & CO. KGAA (DE)

( * ) Notice: Subject to any disclaimer, the term of this patent is extended or adjusted under 35 U.S.C. 154(b) by 11 days.

(21) Appl. No.: 15/735,580

(22) PCT Filed: Sep. 8, 2015

(86) PCT No.: PCT/US2015/048958
§ 371 (c)(1),
(2) Date: Dec. 11, 2017

(87) PCT Pub. No.: WO2017/044078
PCT Pub. Date: Mar. 16, 2017

(65) Prior Publication Data
US 2018/0298929 A1    Oct. 18, 2018

(51) Int. Cl.
*F16M 11/00* (2006.01)
*F16B 2/14* (2006.01)
(Continued)

(52) U.S. Cl.
CPC ............. *F16B 2/14* (2013.01); *A61M 5/1415* (2013.01); *F16B 2/12* (2013.01); *F16B 9/023* (2013.01);
(Continued)

(58) Field of Classification Search
CPC ....... F16M 13/02; F16B 2/02; F16B 2200/40; F16B 12/32; F16B 2200/30
(Continued)

(56) References Cited

U.S. PATENT DOCUMENTS 4,674,722 A    6/1987    Danby et al.
4,844,397 A    7/1989    Skakoon et al.
(Continued)

FOREIGN PATENT DOCUMENTS

EP    0 224 367 B1    11/1991
FR    770 507 A    9/1934
(Continued)

OTHER PUBLICATIONS

Patent Cooperation Treaty, International Preliminary Examination Report for PCT/US2015/048958, dated Mar. 28, 2018 (11 pages).
(Continued)

*Primary Examiner* — Steven M Marsh
(74) *Attorney, Agent, or Firm* — Design IP

(57) ABSTRACT

A clamp device (100) for mounting equipment to a support structure (200) including a base (105) and a slider (110). The base (105) includes a first trough (155) formed in the front side (140) of the base (105) and a second trough (160) formed in the back side (145) of the base (105) and a first coupling element located on the first lateral side (130) and a second coupling element located on the second lateral side (135) of the base (105). Each of the first and second coupling elements extend from near the top end (120) of the base (105) towards the bottom end (125) of the base (105) at an angle relative to the first trough (155). The slider (110) includes a channel (185) on a back side (145) of the slider (110) and corresponding coupling elements within the channel (185) configured to slidingly engage the first and second coupling elements upon association of the slider (110) with the base (105).

36 Claims, 13 Drawing Sheets

(51) Int. Cl.
*F16M 13/02* (2006.01)
*F16M 11/04* (2006.01)
*F16B 9/02* (2006.01)
*A61M 5/14* (2006.01)
*F16B 2/12* (2006.01)

(52) U.S. Cl.
CPC ........ *F16M 11/041* (2013.01); *F16M 13/022* (2013.01)

(58) Field of Classification Search
USPC ......... 248/218.4, 219.1, 219.2, 219.3, 228.1, 248/230.1
See application file for complete search history.

(56) References Cited

U.S. PATENT DOCUMENTS

| | | | |
|---|---|---|---|
| 5,169,106 A | 12/1992 | Rasmussen | |
| 5,332,184 A | 7/1994 | Davis | |
| 5,588,166 A | 12/1996 | Burnett | |
| 5,829,723 A | 11/1998 | Brunner et al. | |
| 7,513,471 B2 * | 4/2009 | Moufflet | A47F 5/0892 248/218.4 |
| 7,866,617 B2 | 1/2011 | Kleitsch | |
| 8,167,259 B2 | 5/2012 | Spang et al. | |
| 8,371,544 B2 * | 2/2013 | Heitmeyer | F16L 3/10 248/229.1 |
| 9,186,294 B1 * | 11/2015 | Free | A61H 7/002 |
| 10,274,110 B1 * | 4/2019 | Liu | F16L 3/1215 |
| 2002/0096610 A1 * | 7/2002 | Fernandez | G09F 7/18 248/218.4 |
| 2002/0162924 A1 * | 11/2002 | Herzog | H01Q 1/1221 248/218.4 |
| 2004/0061032 A1 * | 4/2004 | Bradford | F21V 21/116 248/218.4 |
| 2004/0084582 A1 * | 5/2004 | Kralic | E04H 12/24 248/219.3 |
| 2006/0237940 A1 | 10/2006 | Raidel et al. | |
| 2006/0278781 A1 | 12/2006 | Homra et al. | |
| 2009/0152419 A1 | 6/2009 | Wallace | |
| 2010/0314517 A1 | 12/2010 | Patzer | |
| 2013/0206938 A1 | 8/2013 | Clouser | |

FOREIGN PATENT DOCUMENTS

| | | |
|---|---|---|
| GB | 1 280 979 A | 7/1972 |
| WO | 2013161711 A1 | 10/2013 |

OTHER PUBLICATIONS

Patent Cooperation Treaty, International Search Report and Written Opinion for PCT/US2015/048958, dated May 11, 2016 (pp. 15).

\* cited by examiner

MOUNTING CLAMP DEVICE

RELATED APPLICATION

This application is a national stage application, filed under 35 U.S.C. § 371, of International Application No PCT/US2015/048958, filed Sep. 8, 2015, the entirety of which is incorporated herein by reference.

FIELD

The subject matter described herein relates to securely mounting equipment to a support structure. More specifically, described herein are mounting clamp devices for securely mounting equipment to a support structure using a gravity-assisted wedging action.

BACKGROUND

Mounting medical equipment to an intravenous (IV) pole involves cumbersome and complex hardware that can require special tools. Often the mounting equipment includes numerous mechanical parts that can be costly to manufacture. For example, some mounts for securing medical equipment to an IV pole can include a stationary element and a lead screw having a knob on one end and a clamp pad on an opposite end. The knob of the lead screw must be turned a number of times to urge the clamp pad towards the stationary element to capture the IV pole between them. Although knobs can be used without special tools, this movement involves lots of wrist action to provide sufficient tightening for heavy equipment that leads to user fatigue and injuries. Additionally, turning the knob multiple rotations to reach the size of the pole takes time and clamping force is limited by the user's strength and can therefore be insufficient for some medical equipment that is particularly heavy. Insufficient clamping force can result in patient injury and/or equipment damage.

SUMMARY

In a first aspect, a clamp device for mounting equipment to a support structure includes a base having opposing front and back sides, opposing top and bottom ends, and opposing first and second lateral sides. The base includes a first trough formed in the front side of the base and a second trough formed in the back side of the base; and a first coupling element located on the first lateral side and a second coupling element located on the second lateral side of the base. Each of the first and second coupling elements extend from near the top end of the base towards the bottom end of the base at an angle relative to the first trough. The clamp device includes a slider having a channel on a back side of the slider and corresponding coupling elements within the channel configured to slidingly engage the first and second coupling elements of the base upon association of the slider with the base.

In some variations, the slider reversibly and alternatingly associates with the base such that the corresponding coupling elements within the channel slidingly engage the first and second coupling elements of the base in a first coupled configuration by sliding downwards from the top end of the base towards the bottom end of the base when the first trough faces the channel and in a second coupled configuration by sliding downwards from the bottom end of the base towards the top end of the base when the second trough faces the channel. The first trough and the channel when in the first coupled configuration and the second trough and the channel when in the second coupled configuration can collectively form a space between the base and the slider that narrows as the slider moves downwards relative to the base. The space can be sized to accommodate a support structure. The support structure can have an outer diameter in a range of about 0.5 inches to about 1.25 inches. The slider can urge the support structure against the first trough in the first coupled configuration as the slider moves downwards towards the bottom end of the base and the space is narrowed. The slider can urge the support structure against the second trough in the second coupled configuration as the slider moves downwards towards the top end of the base and the space is narrowed. The first trough can have a shape configured to accommodate a support structure having a first outer diameter and the second trough has a shape configured to accommodate a support structure having a second outer diameter. The first outer diameter can be larger than the second outer diameter. The first trough and the second trough can be v-shaped. The base can contact a first side of the support structure and the slider can contact a second side of the support structure upon association of the slider with the base.

The device can further include one or more compliant elements coupled to one or more regions of the base. The one or more compliant elements can include an elastomeric over-mold coupled within the first and second troughs. The device can further include a tether having a first end coupled to a region of the base and a second end coupled to a region of the slider. The coupling elements of the base can be a pair of tracks and the corresponding coupling elements within the channel of the slider can be a pair of grooves. The corresponding coupling elements within the channel can extend at an angle that is the same as the angle as the first and second coupling elements of the base. The angle can be between about 10 degrees and about 15 degrees. The slider can include a mounting feature on a front side of the slider. The base can have a longitudinal axis extending between the top and bottom ends. The first and second troughs can extend parallel to one another and parallel to the longitudinal axis. The first trough can be formed in the front side of the base and the second trough can be formed in the back side of the base such that they each extend from the top end of the base to the bottom end of the base.

In an interrelated aspect, disclosed is another implementation of a clamp device for mounting equipment to a support structure. The clamp device includes a base having opposing front and back sides, opposing top and bottom ends, and opposing first and second lateral sides. The base includes a first trough formed in the front side of the base and a second trough formed in the back side of the base. The base includes a first coupling element located on the first lateral side and a second coupling element located on the second lateral side of the base. Each of the first and second coupling elements extend from near the top end of the base towards the bottom end of the base at an angle relative to the first trough.

In an interrelated aspect, disclosed is equipment for mounting onto a support structure. The equipment includes a housing and a slider feature integrated with the housing. The slider feature includes a first arm projecting outward from a first region of the housing and having an inner surface and a second arm located a distance away from the first arm and projecting outward from a second region of the housing parallel to the first arm. The second arm has an inner surface facing the inner surface of the first arm. The slider feature includes a channel located between the first arm and the second arm sized to receive at least a portion of an elongate support structure. The slider feature also includes a first coupling element located on the inner surface of the first arm and a second coupling element located on the inner surface of the second arm. Each of the first and second coupling elements extend at an angle from near a top end of the first and second arms towards a bottom end of the first and second arms.

In an interrelated aspect, disclosed is another implementation of a mounting clamp system. The system includes a base having opposing front and back sides, opposing top and bottom ends, and opposing first and second lateral sides. The base has a first trough formed in the front side of the base and a second trough formed in the back side of the base. The base has a first coupling element located on the first lateral side and a second coupling element located on the second lateral side of the base. Each of the first and second coupling elements extends from near the top end of the base towards the bottom end of the base at an angle relative to the first trough. The system also includes equipment having a slider feature integrated with a housing of the equipment. The slider feature includes a first arm projecting outward from a first region of the housing and having an inner surface. The slider feature includes a second arm located a distance away from the first arm and projecting outward from a second region of the housing parallel to the first arm. The second arm has an inner surface facing the inner surface of the first arm. The slider feature includes a channel located between the first arm and the second arm sized to receive at least a portion of an elongate support structure. The slider feature includes a third coupling element located on the inner surface of the first arm and a fourth coupling element located on the inner surface of the second arm. Each of the third and fourth coupling elements extend from near a top end of the first and second arms towards a bottom end of the first and second arms such that the third coupling element slidingly engages the first coupling element and the fourth coupling element slidingly engages the second coupling element upon association of the slider feature with the base.

The details of one or more variations and implementations of the clamp device and methods are set forth in the accompanying drawings and the description below. Other features and advantages will be apparent from the description and drawings, and from the claims.

BRIEF DESCRIPTION OF THE DRAWINGS

These and other aspects will now be described in detail with reference to the following drawings.

Like reference symbols in the various drawings indicate like elements.

DETAILED DESCRIPTION

Described herein are devices, systems and methods for securely mounting equipment to a support structure. More specifically, described herein are clamp devices for securely mounting equipment to a support structure. In addition, the clamp devices incorporate a gravity-assisted wedging action to securely mount the equipment. The equipment mounted as well as the support structure to which the equipment is mounted can vary and should not be limiting. The equipment can include medical devices such as drug delivery systems, patient monitors, or other medical equipment for mounting on a support structure. The devices described herein can mount the equipment to a wide range of supports that can be found in a variety of locations. The equipment can also include non-medical equipment such as computer monitors or TV screens, or other items that may need to be mounted during use. The support structure can be a structure such as an upright cylindrical IV pole or similar structure. It should be appreciated, however, that the support structure need not be cylindrical or upright to be used with the clamp device. The devices described herein can provide sufficient clamping force for mounting heavy and expensive equipment and are quick to install and remove, ergonomic and simple in operation for a wide range of support structure sizes. The devices described herein prevent issues of user fatigue, increase patient safety, are relatively simple and have a reduced cost of manufacturing.

Figure 1:
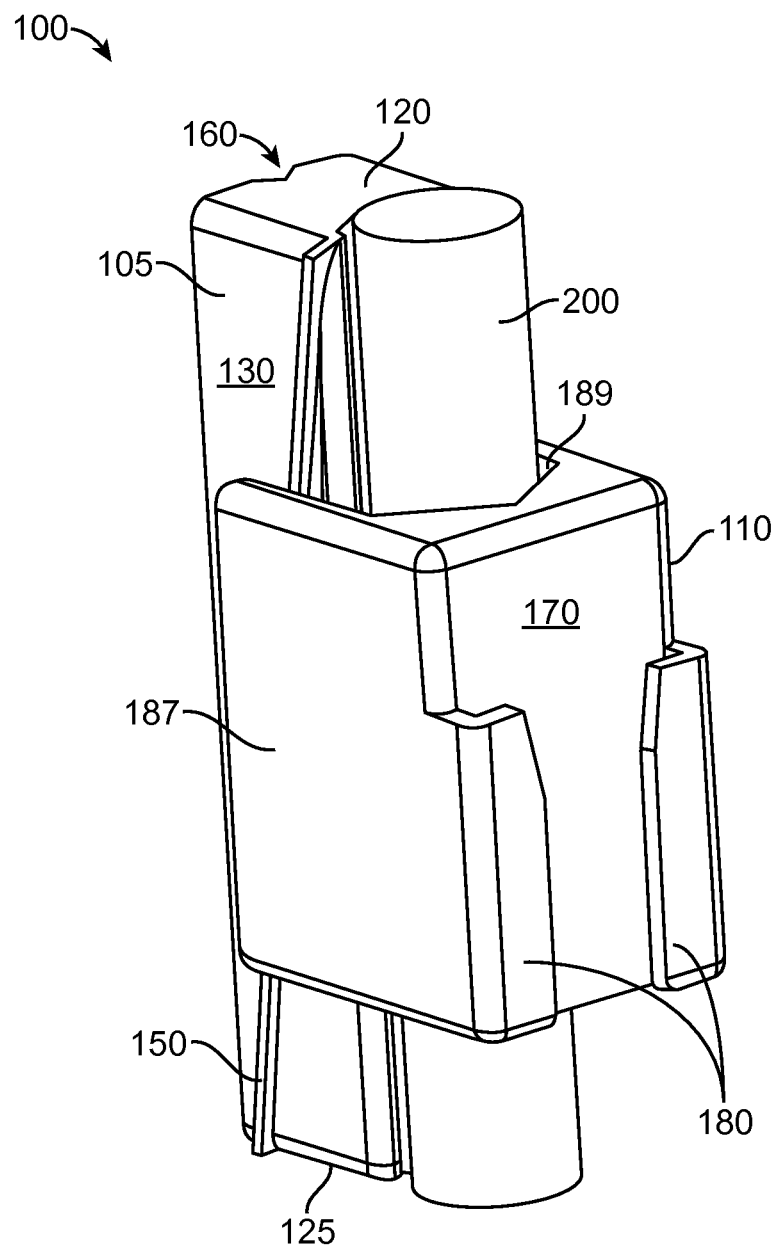
FIG. 1 shows an implementation of a clamp device in a coupled configuration with a support structure positioned within the clamp device.
Figure 2A:
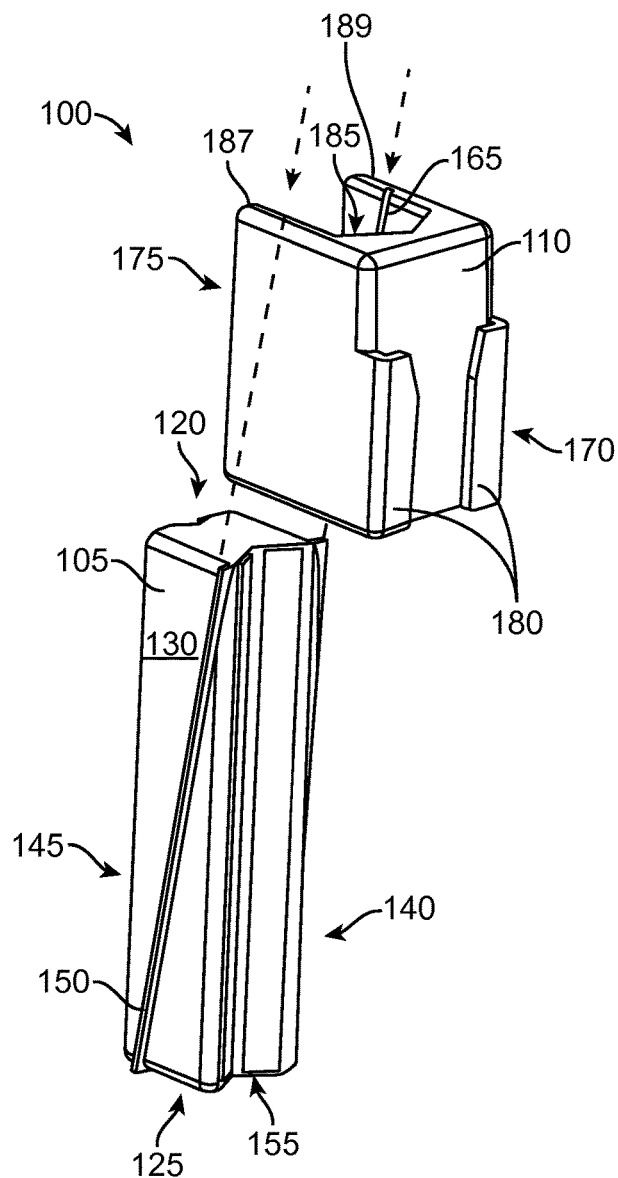
FIGS. 2A and 2B show the clamp device of FIG. 1 in an uncoupled configuration with and without the support structure, respectively.
Figure 2B:
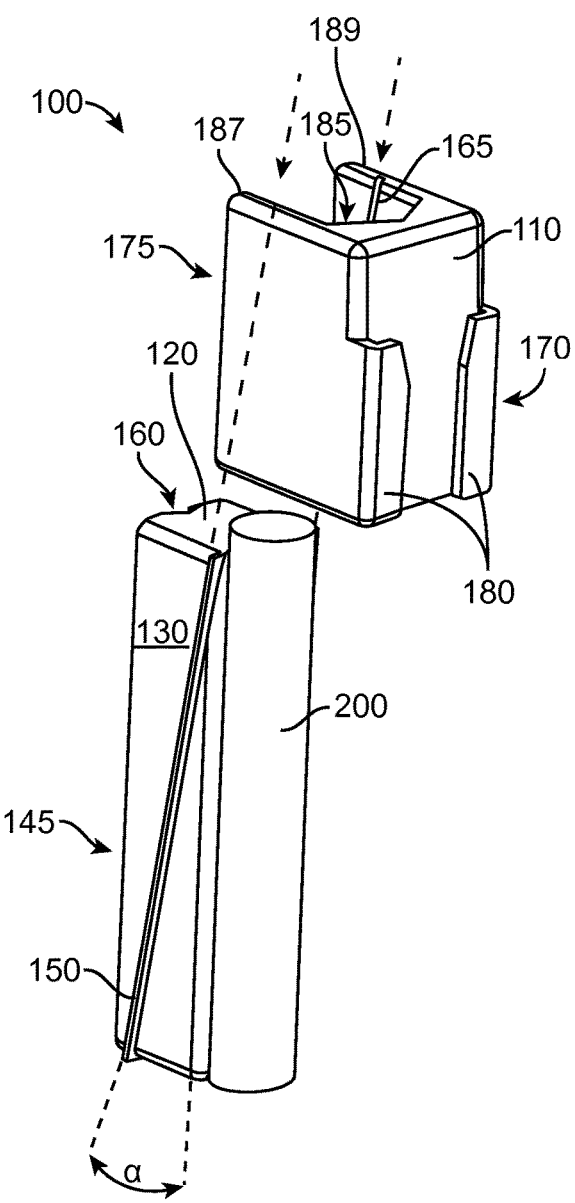

FIG. 1 shows an implementation of a clamp device 100 in use with a support structure 200. FIG. 1 shows the clamp device in a coupled configuration with the support structure 200 positioned within the clamp device 100 and FIGS. 2A and 2B show the clamp device 100 in an uncoupled configuration with and without the support structure 200, respectively. The clamp device 100 can include a base 105 and a slider 110. The base 105 can be a stationary piece configured to contact or be positioned onto a first side of a support structure 200 and the slider 110 can be a moveable piece configured to contact or be positioned onto a second side of the support structure 200 such that the support structure 200 is captured between the base 105 and the slider 110 when the clamp device is in a coupled configuration. It should be appreciated however that during use, both the base 105 and the slider 110 can be moveable relative to one another. The slider 110 can slidingly engage the base 105, for example, from an upper end of the base 105 downwards capturing the support structure 200 within the clamp device 100 (see FIGS. 2A-2B). The sliding engagement between the slider 110 and the base 105 is reversible such that equipment can be mounted as well as removed. The slider 110 can slide onto the base 105 from an upper end and be urged downwards towards a lower end of the base 105 therein urging the support structure against a trough as the slider moves downwards towards the bottom end of the base 105 and the space between them is narrowed. The coupling of the slider 110 onto the stationary base 105 can provide the tightening force for mounting the equipment to the support structure 200 as will be described in more detail below. Because the slider 110 couples onto the base 105 in a downward direction, the weight of the equipment being mounted can aid in providing further clamping force inward around the support structure 200. The gravity-assisted clamping force is more user-friendly in that it does not depend upon a user's strength to provide further tightening of the device 100 onto the support structure 200, such as by applying torque by wrist action.

The base 105 can be a generally rectangular element having opposing top end 120 and bottom end 125, opposing first lateral side 130 and second lateral side 135, as well as opposing front 140 and back 145 sides (see FIG. 3, FIG. 4A, FIGS. 5B, and 7B). The base 105 can include a coupling element configured to be associated with a corresponding coupling element on the slider 110. A first coupling element can be located on the first lateral side 130 and a second coupling element can be located on the second lateral side 135. The first and second coupling elements can extend from near the top end 120 towards the bottom end 125 of the base at an angle, as will be described in more detail below. The slider 110 can include corresponding coupling elements configured to slidingly engage the first and second coupling elements of the base 105 upon association of the slider 110 with the base 105. The slider 110 can reversibly associate with the base 105 such that the corresponding coupling elements of the slider 110 slidingly engage the first and second coupling elements of the base 105 by sliding, for example, downwards from the top end 120 of the base 105 towards the bottom end 125 of the base 105, urging the support structure 200 against the base 105 as the slider 110 moves relative to the base 105.

Figure 3:
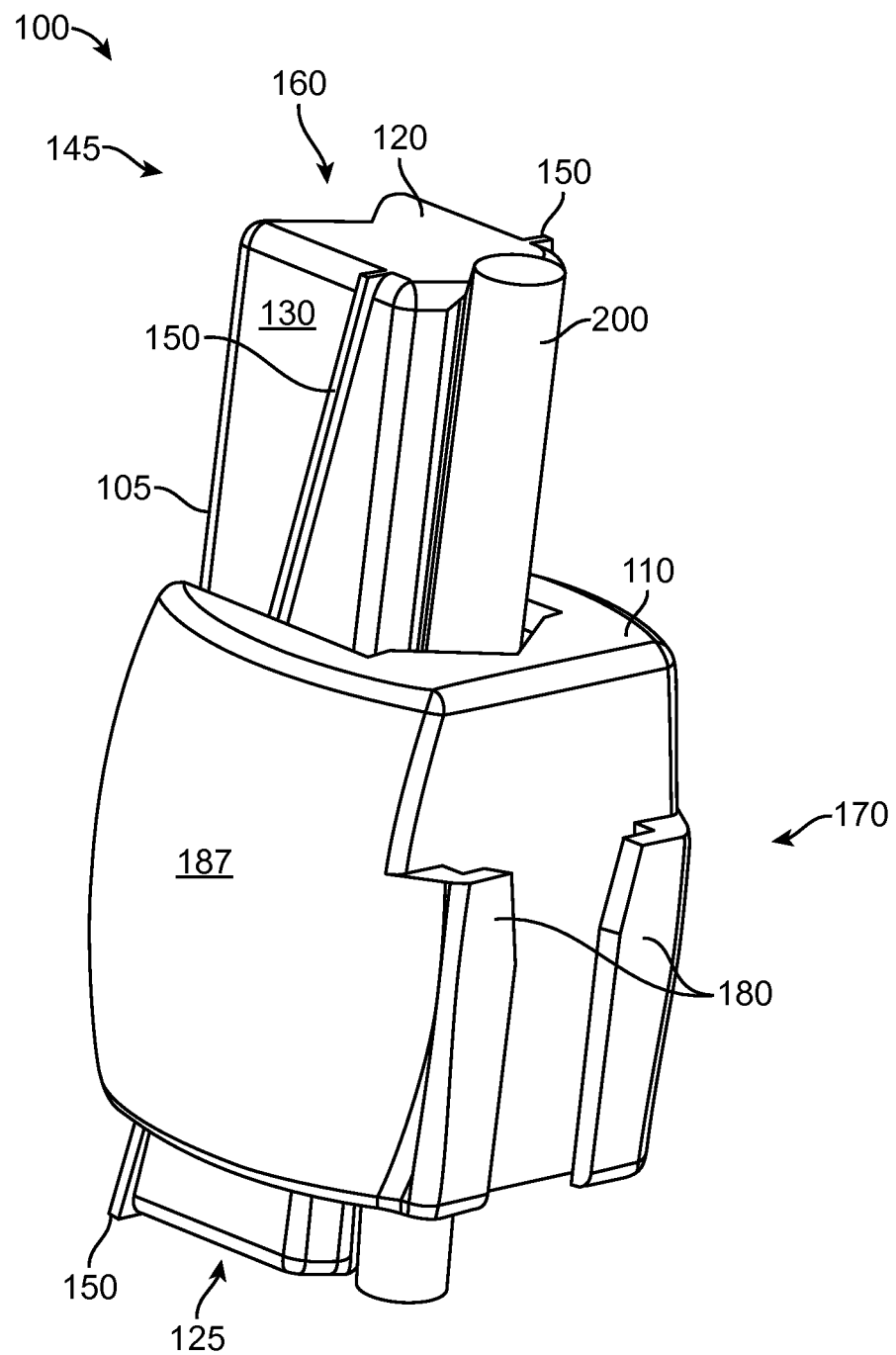
FIG. 3 shows another implementation of a clamp device in a coupled configuration with a support structure positioned within the clamp device.
Figures 4A, 4B:
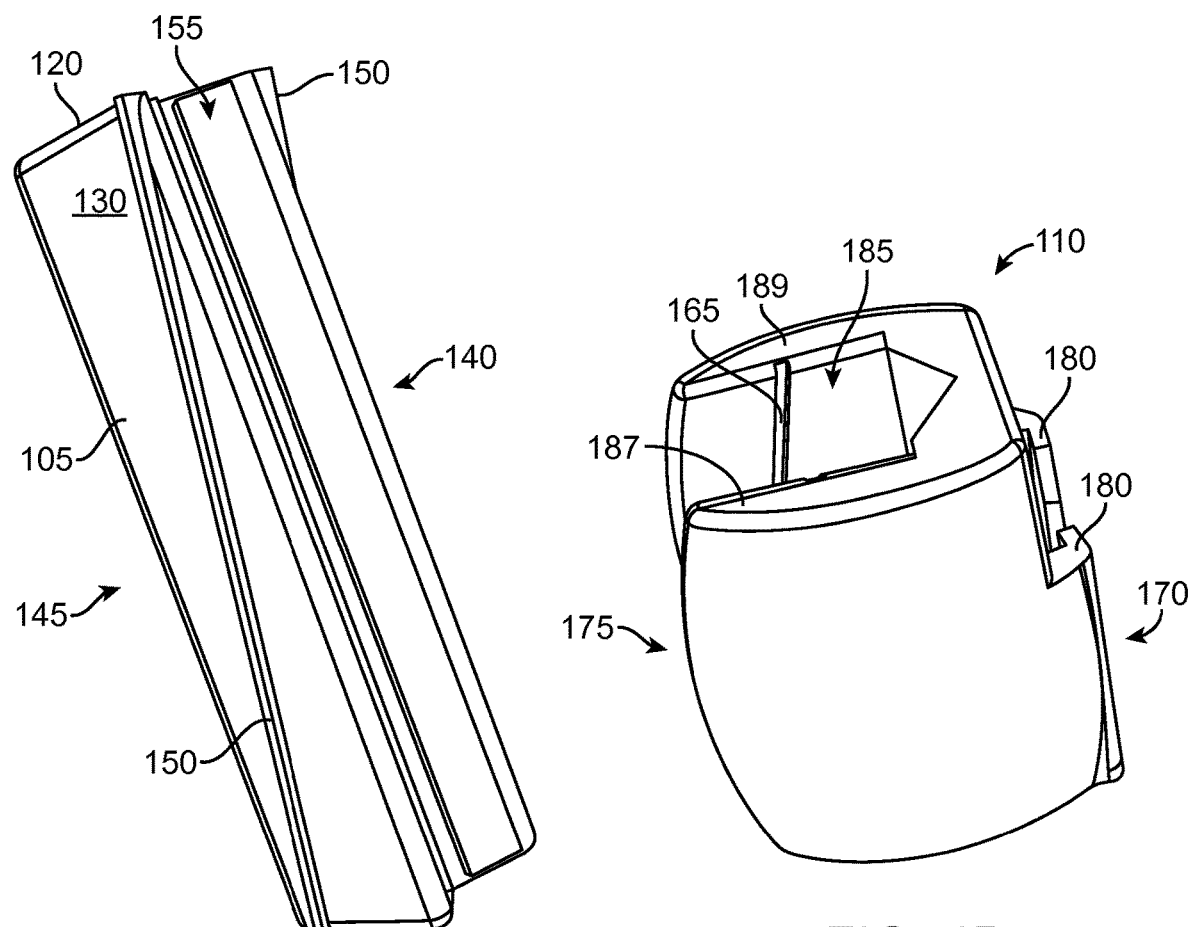
FIGS. 4A and 4B show the base and slider of the clamp device of FIG. 3 in an uncoupled configuration.
Figure 5A:
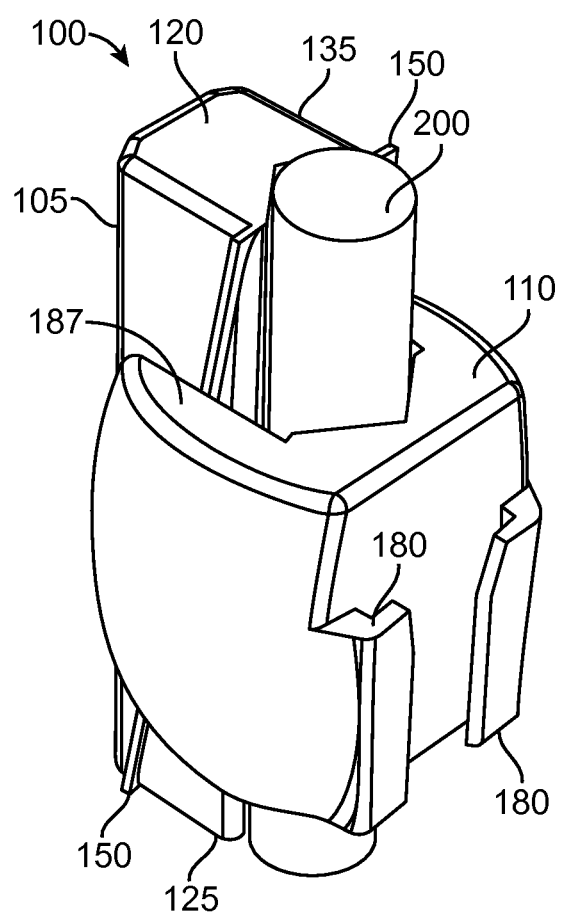
FIG. 5A shows another implementation of a clamp device in a coupled configuration with a support structure positioned within the clamp device.
Figure 5B:
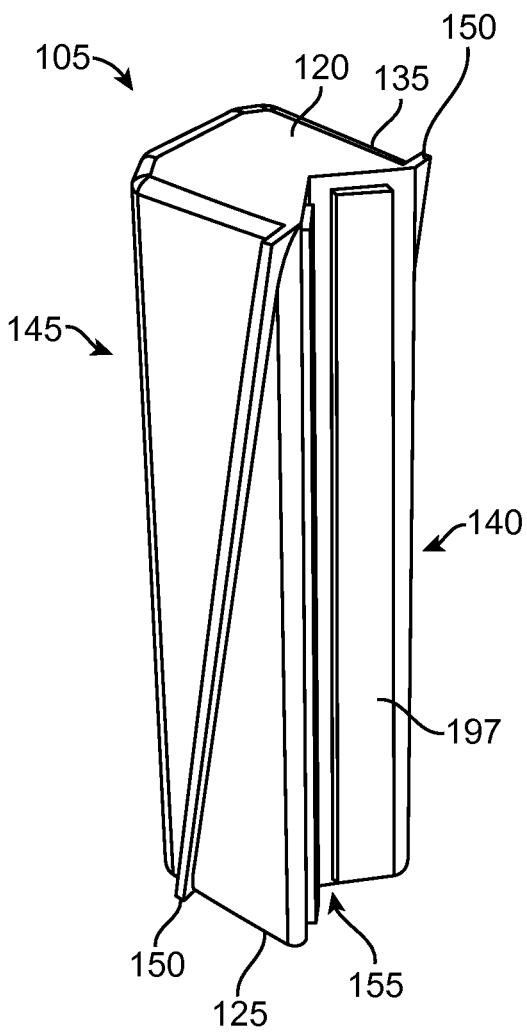
FIG. 5B shows the base of the clamp device of FIG. 5A.
Figure 6A:
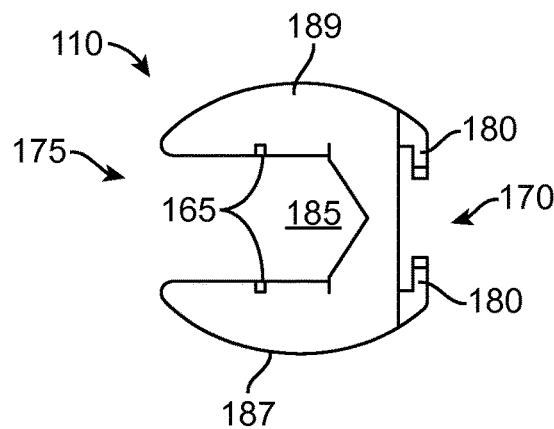
FIG. 6A shows a top end view of the slider of the clamp device of FIG. 5A.
Figure 6B:
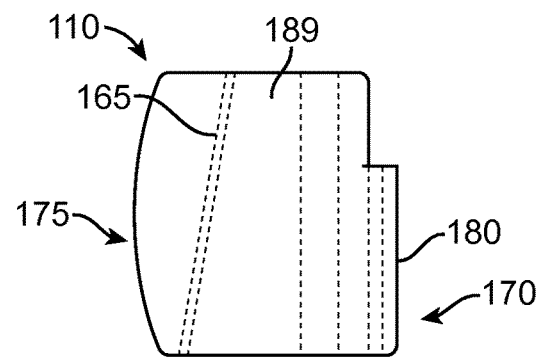
FIG. 6B shows a side, hidden view of the slider of FIG. 6A.

The coupling element of the base 105 can be a pair of angled tracks 150 and the corresponding coupling elements within the channel of the slider can be a pair of grooves 165 (see FIG. 3). A first track 150 can be located on the first side 130 and a second track 150 can be located on the second side 135 of the base 105. The tracks 150 can project away from the sides 130, 135 of the base 105 such that they form a flange that can be captured by the corresponding coupling element, such as a pair of corresponding grooves 165 (see FIG. 6A), as will be described in more detail below. The cross-sectional shape of each of the pair of tracks 150 and grooves 165 are corresponding, but can vary. The cross-sectional shape of each of the pair of tracks 150 and grooves 165 can be generally square, rectangular, rounded, triangular, or other geometry. The corresponding shapes of the tracks and grooves can also be a keyed coupling between the base 105 and the slider 110. For example, the grooves 165 can have an omega shape such that the outer regions of the grooves 165 mate with corresponding flanges on the tracks 150 to improve the grip provided by the coupling. In other implementations, the device can incorporate a tongue and groove arrangement. In some implementations, the upper and lower regions of the grooves 165 can have a chamfer to improve entry of the tracks 150 into the grooves 165.

It should be appreciated that the base 105 and the slider 110 couple together using corresponding coupling elements configured to associate in a sliding manner. The configuration of the respective coupling elements can vary. For example, the tracks 150 can be part of the slider 110 rather than the base 105 and the grooves 165 can be part of the base 105 rather than the slider 110. Although the tracks 150 and grooves 165 are described as being part of the base 105 and the slider 110, respectively, it should be appreciated that the reverse is possible.

Each track 150 can originate from near the top end 120 of the base 105 and extend along an angle $\alpha$ towards the bottom end 125 of the base 105 as will be described in more detail below (see FIGS. 2B, 4A, 5B, and 7B). In some implementations, the tracks 150 extend from near the front side 140 of the base 105 at the top end 120 towards the back side 145 of the base 105 at the bottom end 125 such that the tracks 150 run generally diagonally along the first and second lateral sides 130, 135. The angle $\alpha$ of the tracks 150 and the angle $\alpha$ of the corresponding grooves 165 is generally the same. The angle $\alpha$ can vary. It should be appreciated that the angle $\alpha$ can be relative to a trough within which the support structure 200 is received or to a longitudinal axis of a space within which the support structure is received. In some implementations, the angle $\alpha$ can be between about 5° and about 20°, or between 10° and 15°. In one implementation, the angle $\alpha$ of the track 150 is about 10°. The clamping angle $\alpha$ of about 10° to about 15° can offer an optimal aspect ratio of the dimensions of base 105 and slider 110 to accommodate a desired size range of support structures 200. This clamping angle can also require less user-applied removal force to open the clamp device 100 after the device 100 has been used to support the weight of the equipment. Clamping angles increasing from 15° to 45° can result in aspect ratio changes to the base 105 and slider 110, increasing depth (X) and decreasing length (Y) for desired support structure 200 size range coverage. This can also increase the user-applied removal force to open the clamp device 100 after supporting weight of the equipment.

The base 105 can also include at least one trough 155 located on the front side 140 of the base 105 and configured to receive at least a portion of a support structure 200. The trough 155 can extend from the top end 120 of the base 105 to the bottom end 125 of the base 105. In some implementations, the at least one trough 155 extends parallel to a longitudinal axis of the base 105 between the top end 120 of the base 105 to the bottom end 125 of the base 105. The slider 110 can engage the base 105 by sliding onto the base 105 from the top end 120 of the base 105 capturing the support structure 200 within the trough 155 between the base 105 and the slider 110. The trough 155 can be located along a center of the base front 140. In some implementations, the base 105 can include a first trough 155 and a second trough 160 (see FIGS. 1, 2A-2B, 3, 7A-7B, and 8A-8B). The first trough 155 can be formed along a center of the front side 140 of the base 105 and the second trough 160 can be formed along a center of the opposing back side 145 of the base 105. Thus, the base 105 can be flipped 180° end-over-end such that the second trough 160 faces the support structure 200 and the bottom end 125 is then positioned at the top of the device 100 (see FIG. 8B). In this case, the slider 110 can engage with the base 105 from the bottom end 125 down such that the support structure 200 is captured within the second trough 160. As mentioned above, the first coupling element located on the first lateral side and the second coupling element located on the second lateral side of the base 105 extend from near the top end 120 of the base 105 towards the bottom end 125 of the base 105. The slider 110 can include a channel having corresponding coupling elements within the channel configured to slidingly engage the first and second coupling elements of the base 105 upon association of the slider 110 with the base 105. The slider 110 can reversibly and alternatingly associate with the base 105 such that the corresponding coupling elements within the channel slidingly engage the first and second coupling elements of the base 105 in a first coupled configuration by sliding downwards from the top end 120 of the base 105 towards the bottom end 125 of the base 105 when the first trough 155 faces the channel 185 of the slider 110 and in a second coupled configuration by sliding downwards from the bottom end 125 of the base 105 towards the top end 120 of the base 105 when the second trough 160 faces the channel 185 of the slider 110. The first trough 155 and the channel 185 when in the first coupled configuration (or the second trough 160 and the channel 185 when in the second coupled configuration) collectively form a space 190 between the base 105 and the slider 110 that narrows as the slider 110 moves downwards relative to the base 105. The space 190 is sized to accommodate the support structure 200 having a variety of outer diameters as will be described in more detail below. The first and second troughs 155, 160 can extend parallel to one another and parallel to the longitudinal axis of the base 105.

Each of the troughs 155, 160 of the base 105 can be sized and shaped to receive a support structure 200 having a range of different outer diameters. For example, the outer diameter of the support structure 200 can be in the range of about 0.5 inches to about 1.25 inches. In some implementations, the first trough 155 can be configured to receive a support structure 200 of a first outer diameter and the second trough 160 can be configured to receive a support structure 200 of a second outer diameter, the first outer diameter can be larger than the second outer diameter. The first and second troughs 155, 160 can accommodate a range of outer diameters that overlap (in some implementations, only minimally), or do not overlap such that a wider range of outer diameters of support structures 200 can be accommodated by a single clamp device 100. For example, the first trough 155 can accommodate a range of outer diameters that are about 0.75 inches to about 1.25 inches and the second trough 160 can accommodate a range of outer diameters including about 0.50 inches to about 0.75 inches. This allows for a single clamp device 100 to accommodate support structures within a total range of outer diameters that is between about 0.50 inches to about 1.25 inches while still maintaining a generally small form factor of the clamp device 100, as discussed in more detail below.

The troughs 155, 160 can have a shape configured to accommodate the support structure 200 having a particular outer diameter. In some implementations, one or both of the troughs 155, 160 can be generally v-shaped (see FIG. 7A). It should be appreciated that other geometries are considered herein. For example, one or both of the troughs 155, 160 can also be more rounded such that the troughs 155, 160 forms an arc of a circle. The troughs 155, 160 can have generally the same shape or different shapes. The shape of the support structure 200 received within the trough 155, 160 can vary as well. IV poles are generally cylindrical, however, the clamp device 100 can be used with support structures 200 that are not cylindrical, for example, square, rectangular, octagonal, oval, elliptical, or other cross-sectional shape. It should also be appreciated that the clamp device 100 can be used with a support structure 200 that is extending along angles other than vertical or upright, such as horizontal, diagonal or another angle in between.

One or both of the troughs 155, 160 can be generally v-shaped such that it contacts only a portion of the support structure 200. For example, if the support structure 200 is a cylindrical pole, a first side of the "v" can contact the support structure 200 near a first quadrant and a second side of the "v" can contact the support structure 200 near a second quadrant adjacent the first quadrant such that the troughs 155, 160 contacts the support structure 200 on only a first side of the support structure 200. The base 105 can contact a first side of the support structure 200 and the slider 110 can contact a second side of the support structure 200 upon association of the slider 110 with the base 105. In some implementations, the only point of contact is made between one of the troughs 155, 160 and the support structure 200. The depth and/or angle of the "v" formed by the trough 155, 160 can vary as well such that the trough 155, 160 is configured to receive support structure 200 having various ranges in outer diameter. Generally, the shape of the troughs 155, 160 is such that the base 105 extends around at least a portion of the outer diameter of the support structure, for example, between about 10° to about 95° of the outer diameter of the support structure 200. The base 105 can extend around the outer diameter of the support structure 200 only by at least about 10°, 15°, 20°, 25°, 30°, 35°, 40°, 45°, 50°, 55°, 60°, 65°, 70°, 75°, 80°, 85°, 90°, or 95°. Generally, the base 105 does not extend around the outer diameter of the support structure 200 greater than 120° such that only the sides of the "v" of the v-shaped trough 155, 160 contact the support structure 200. The flat surfaces of the v-shaped troughs 155, 160 can contact only a limited surface of the outer diameter of the support structure 200.

Figure 7A:
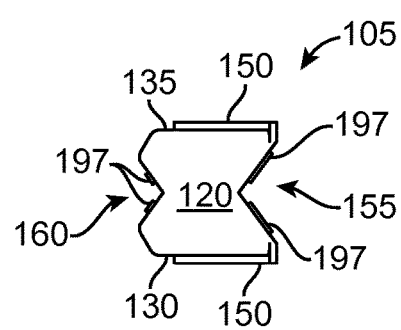
FIG. 7A shows a top end view of the base of the clamp device of FIG. 3.
Figure 7B:
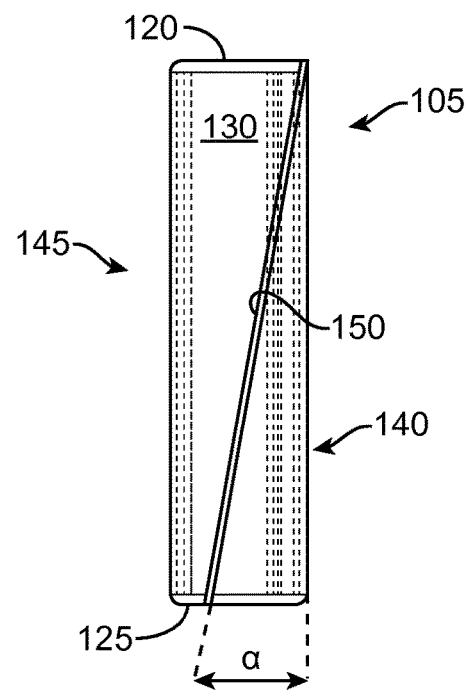
FIG. 7B shows a side view of the base of the clamp device of FIG. 3.

In some implementations and as best shown in FIG. 7A-7B, an upper end of the angled tracks 150 can be positioned on the sides 130, 135 of the base 105 such that the upper end of the angled tracks 150 are located immediately adjacent the upper end of the trough 155. The upper end of the angled tracks 150 can be located a minimal distance away from the front 140 such that the angled tracks 150 originate at or near the outer edges of the first "v" shaped trough 155. A lower end of the angled tracks 150 can be located a larger distance away from the front 140 of the base 105 compared to the upper end, but a minimal distance away from the back 145 such that the angled tracks 150 terminate at or near the outer edges of the second "v" shaped trough 160. This allows the base 105 to be used reversibly with the slider 110. The base 105 can be flipped end-over-end 180° and oriented relative to the support structure 200 such that the top end 120 is located at the bottom and the bottom end 125 is located at the top and the first trough 155 faces the back and the second trough 160 faces the front such that it can receive the support structure 200. In other words, the top and bottom of the base 105 can be reversed and a trough of the base 105 originally facing towards the support structure 200 then faces away from the support structure 200 and the trough originally facing away from the support structure 200 then faces towards the support structure 200. The reversibility of the base 105 relative to the slider 110 and presence of two troughs 155, 160 accommodating differing ranges of outer diameter support structures 200 keeps the form factor generally small and provides a universality to the clamp device 100 for a wide range of mounting purposes. Further, the reversibility of the base 105 relative to the slider 110 and the presence of the two troughs 155, 160 also reduces the number of components needed to accommodate the differing diameter ranges.

As mentioned above, the slider 110 can tighten the clamp device 100 to the support structure 200. The slider 110 can include a front side 170 configured to receive at least a portion of a piece of equipment to be mounted and a back side 175 configured to engage with the base 105 (see FIGS. 2A-2B, FIG. 4B, FIG. 5A, and FIGS. 6A-6B). The front side 170 can have a mounting feature 180. It should also be appreciated that the mounting feature 180 need not be limited to the front side 170 of the slider 110. For example, in some implementations, the mounting feature 180 can be on another part of the slider 110. A mounting feature 180 also can be incorporated on a portion of the base 105 or on both the slider 110 and the base 105. The configuration of the mounting feature 180 can vary including a dovetail mount as shown or any of a variety of universal mounts.

The back side 175 can include a channel 185 extending through it from one end of the slider 110 to the opposite end of the slider 110 such that a first arm 187 projects outward from the front 170 of the slider 110, for example perpendicularly, forming one side of the channel 185. A second arm 189 projects outward from the front 170 of the slider 110, for example perpendicularly, forming an opposite side of the channel 185. The arms 187, 189 can extend over at least a portion of the sides 130, 135 of the base 105 when the slider 110 is engaged with the base 105. An outer surface of the arms 187, 189 can have various shapes. In some implementations, the particular shape selected can have an aesthetic and/or ergonomic purpose. For example, the outer surface of the arms 187, 189 can be rounded as shown in FIG. 3 or more angular or flat as shown in FIG. 1. The outer surface of the arms 187, 189 can also incorporate one or more textured features to improve grip of the slider 110. An inner surface of the first arm 187 can contact the first side 130 of the base 105 and an inner surface of the second arm 189 can contact the second side 135 of the base 105. The inner surfaces of arms 187, 189 of the slider 110 can each have a groove 165 (see FIG. 6A). Each groove 165 can extend at an angle α' away from the front side 170 of the slider 110 such that a first end region of each groove 165 can be located a first distance from the front side 170 of the slider 110 and a second end region of each groove 165 can be located a second distance from the front side 170 of the slider 110. As mentioned above, the pair of angled grooves 165 of the slider 110 are configured to receive and engage with the angled tracks 150 of the base 105 upon engaging the slider 110 onto the base 105. Thus, angle α' of the grooves 165 generally matches angle α of the tracks 150 (see FIG. 6B).

Figure 9A:
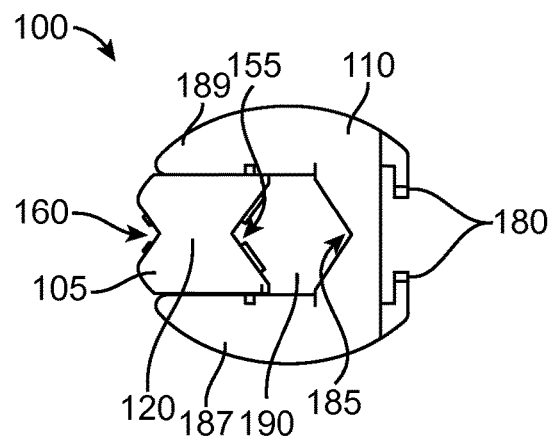
FIG. 9A shows a top end view of a clamp device in a coupled configuration.
Figure 9B:
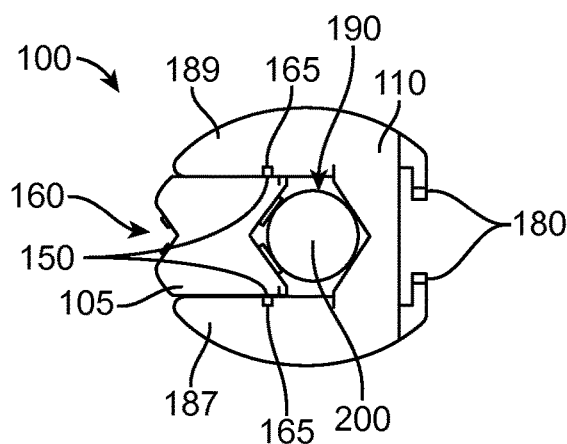
FIG. 9B shows a top end view of the clamp device of FIG. 9A having a support structure positioned within the space collectively formed by a first trough of the base and a channel of the slider.
Figure 9C:
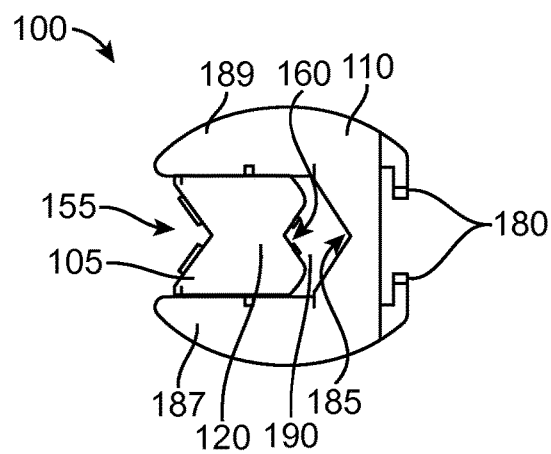
FIG. 9C shows a top end view of a clamp device in a coupled configuration.
Figure 9D:
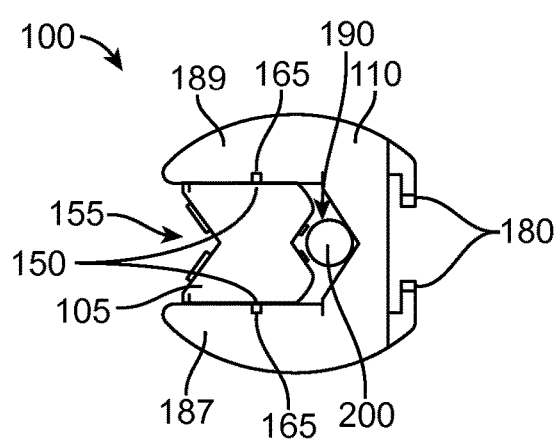
FIG. 9D shows a top end view of the clamp device of FIG. 9C having a support structure positioned within the space collectively formed by a second trough of the base and a channel of the slider.

An inner region of the channel 185 can face the trough 155 of the base 105 and collectively form the space 190 between the base 105 and the slider 110 within which the support structure 200 can extend. The slider 110 can engage with the base 105 from the top end 120 down such that the support structure 200 is captured within the space 190 collectively formed between the trough 155 of the base 105 and the channel 185 of the slider 110. As the slider 110 slides relative to the stationary base 105 from the top end 120 towards the bottom end 125 and the grooves 165 receive the tracks 150 of the base 105, the association between the slider 110 and the base 105 becomes tighter and the space 190 between the slider 110 and the base 105 narrows. The narrowing of the space 190 forms a compressive grip on the support structure 200 positioned within the space 190 between the slider 110 and the base 105. In some implementations, the inner region of the channel 185 is v-shaped and the trough 155 is also v-shaped such that the space 190 formed between the base 105 and the slider 110 has a polygonal geometry (see FIG. 9A). The size of the space 190 can change upon further association of the slider 110 onto the base 105 such that the clamping force of the device 100 onto the support structure 200 changes. For example, as the slider 110 moves downward onto the base 105, the space 190 between the base 105 and the slider 110 decreases until the inner surfaces of the channel 185 and inner surfaces of the trough 155 contact and wedge against the outer surface of the support structure 200 (see FIG. 9B). Because downward travel of the slider 110 relative to the base 105 causes tightening pressure by the device 100 on the support structure 200, the clamping effect provided by the clamp device 100 can be assisted by gravity and the weight of the equipment mounted on the front side 170 of the slider 110 by the mounting feature 180, which urges the slider 110 further downward. Description relating to the trough 155 shown in FIGS. 9A and 9B applies also to trough 160 shown in FIGS. 9C and 9D throughout. Thus, where trough 155 is described it should be appreciated that the same description applies to trough 160 and vice versa.

The weight of the equipment being mounted, the angle of the tracks 150, the shape of the trough 155 and the overall length of the base 105 can have an interrelated relationship. For example, if the angle α of the tracks 150 is too steep the clamping effect may be insufficient or not provide enough holding force for equipment that is of a certain weight although it could be useful for lighter pieces of equipment. Also, a base 105 having a single trough 155 shaped for accepting support structures 200 of varying sizes may have a base 105 that is longer than, for example, a version of the base 105 having dual troughs 155, 160.

In some implementations, the width of the sides 130, 135 of the base 105 can be between about 35 mm and about 40 mm and the length of the front 140 and back 145 of the base 105 can be between about 140 mm and about 150 mm. The width of the slider 110 from front side 170 to back side 175 can be between about 60 mm and about 65 mm. The width of the channel 185 between the arms 187, 189 can be between about 30 mm and about 40 mm. In some implementations, the length of the slider 110 from top end to bottom end can be between about 75 mm to about 80 mm.

The base 105 and/or the slider 110 can be formed of a variety of one or more materials. The base 105 and slider 110 can be formed of a material that is generally rigid such that the device 100 is suitable for holding heavier objects as well as lighter weight objects. The materials can include one or more plastics such as acrylic, PMMA, ABS, Nylon, PLA, polycarbonate, PES, PEEK, PE, PPO, PPS, PP, PA6, PA12, PBT, co-polyester, polystyrene, PVC, or other polymers and combinations thereof. The materials can also include one or more metals such as aluminum.

The base 105 can include one or more compliant elements 197 coupled to one or more regions of the base 105 (see FIGS. 7A-7B). For example, one or more compliant elements 197 can be coupled within the one or more troughs 155, 160 to provide a firm grip to the support structure 200. The compliant elements 197 can be over-molded. In some implementations, the trough 155, 160 can include one or more ridges 198 configured to accept an elastomeric coating. The compliant elements 197 can provide enhanced grip for capturing the support structure 200 within the space 190. The compliant elements 197 can provide anti-slip properties to the troughs 155, 160. The compliant elements 197 can be any of a variety of materials including a variety of plastics and elastomeric materials including, but not limited to various polymers, rubbers, silicones, EVA, and the like. In some implementations, the compliant elements 197 can include a TPU elastomeric over-mold. The materials can have molded features that further improve their grip.

Figure 8A:
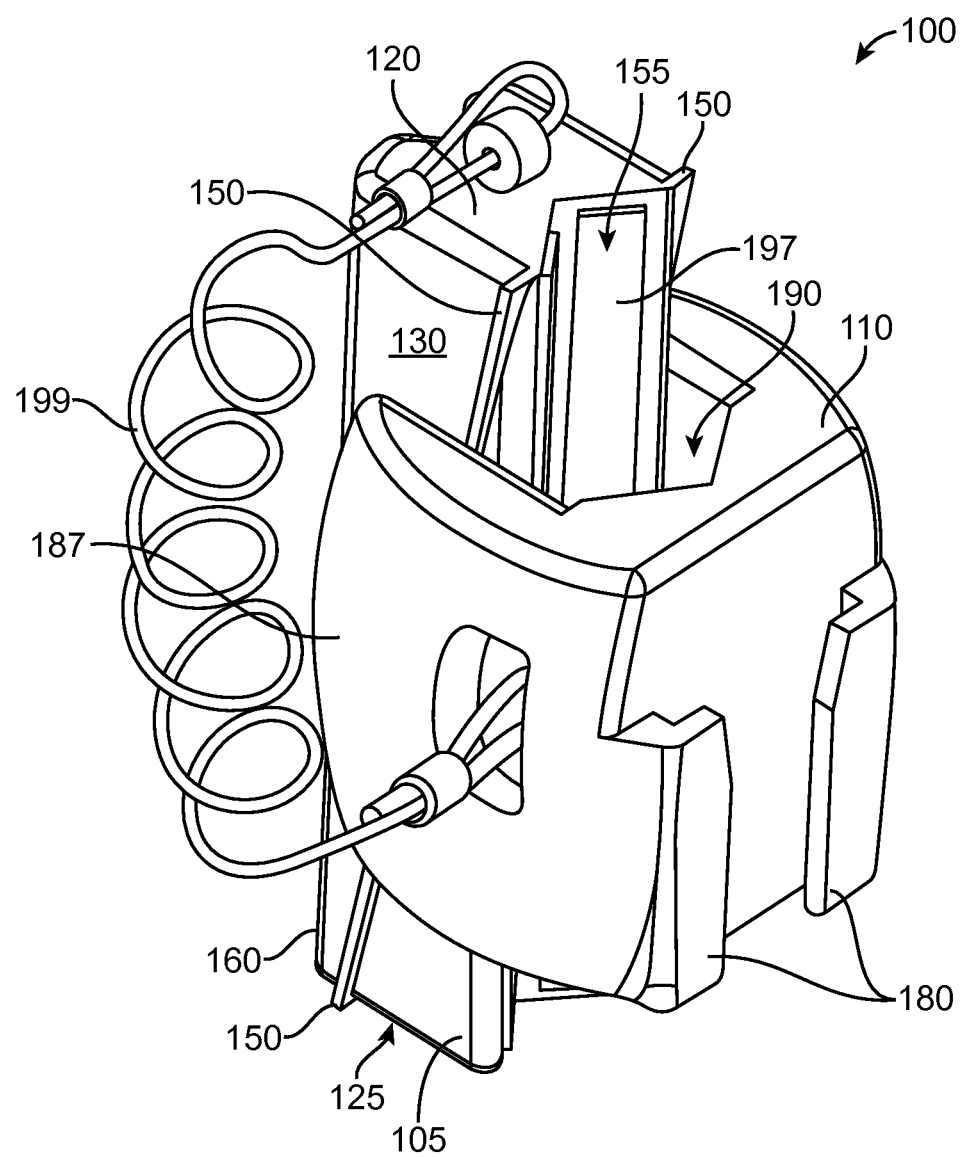
FIG. 8A shows another implementation of a clamp device in a coupled configuration using a first trough for a support structure having a first diameter.
Figure 8B:
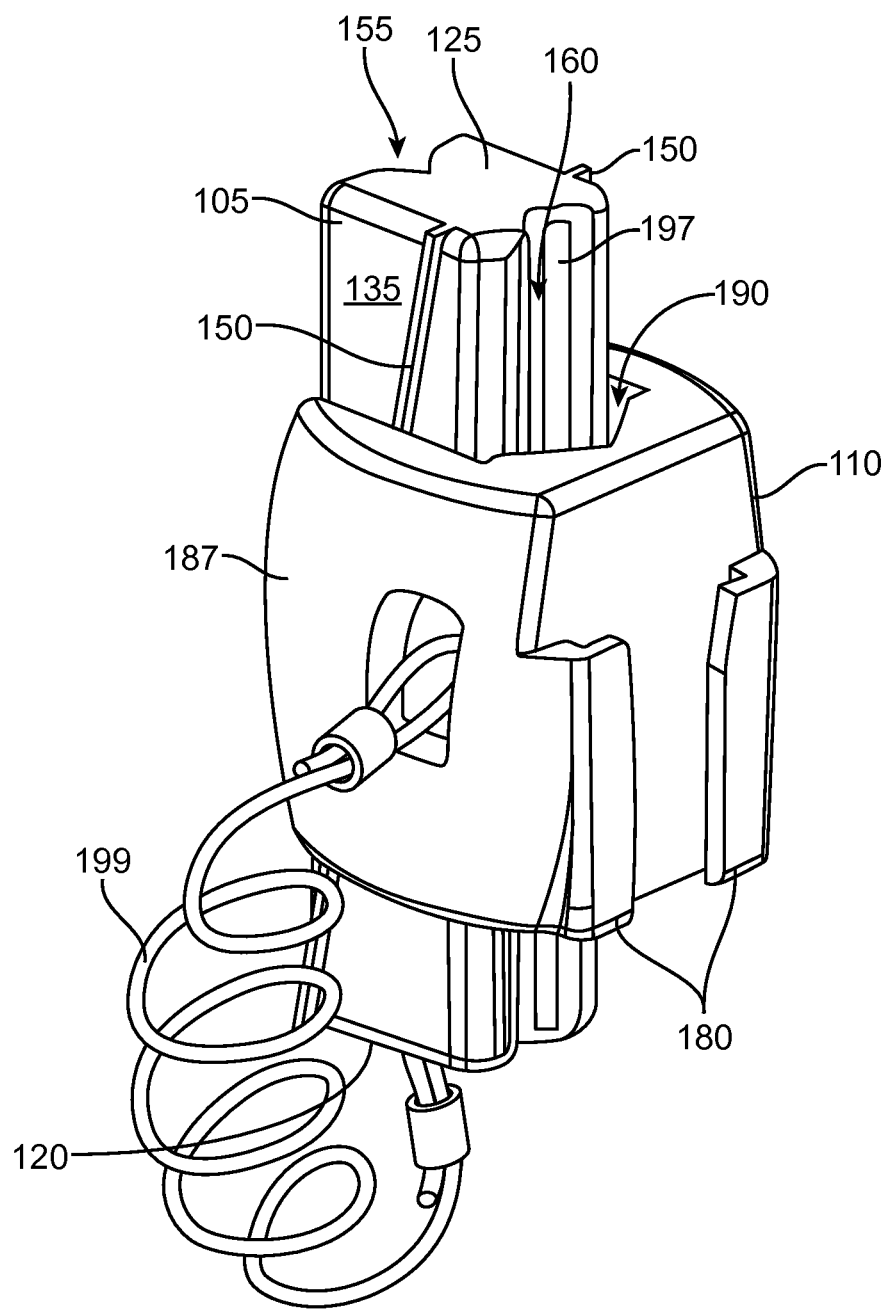
FIG. 8B shows the clamp device in a coupled configuration using a second trough for a support structure having a second diameter.

The base 105 and the slider 110 can be additionally attached to one another, for example, by a tether 199 (see FIG. 8A-8B). The tether 199 can be attached at a first end to a region of the base 105 and at a second end to a region of the slider 110. The tether 199 can vary including, for example, a flexible tether, a bungee coil, wire, metal, plastic, cloth, or other type of tether. The base 105 and slider 110 can be attached by the tether 199 when not in use so as not to lose one portion of the clamp device 100.

Figure 10:
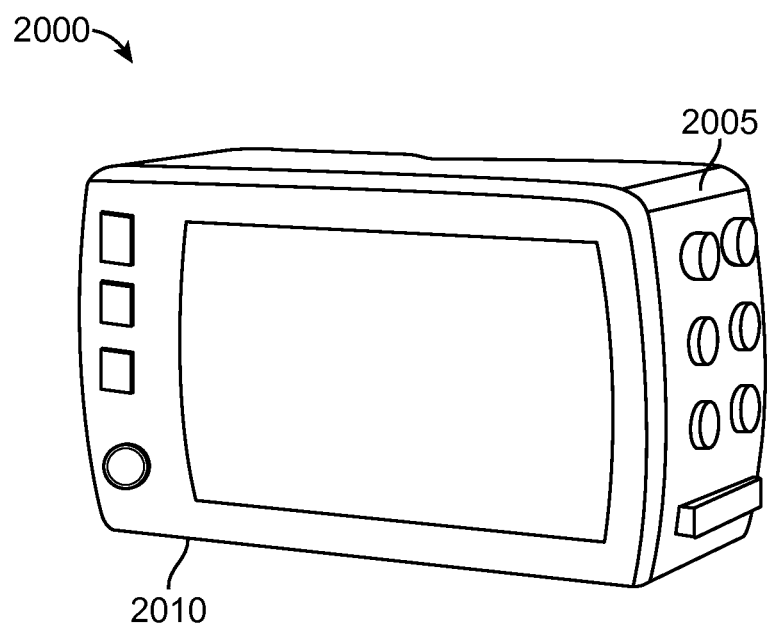
FIG. 10 shows a perspective view of equipment that can be mounted using the clamp devices described herein.
Figure 11:
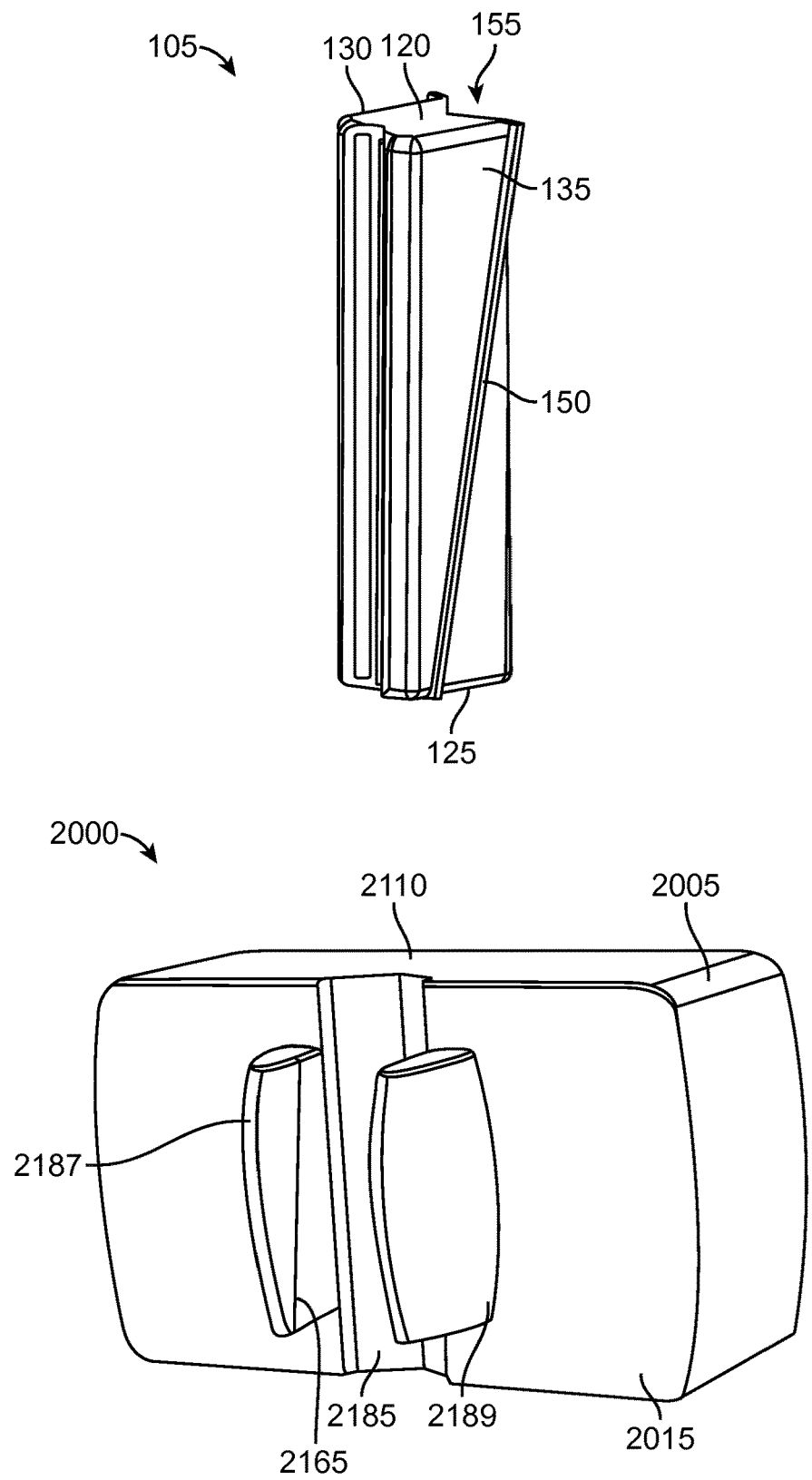
FIG. 11 is an exploded view of the equipment of FIG. 10 and the clamp device.
Figure 12:
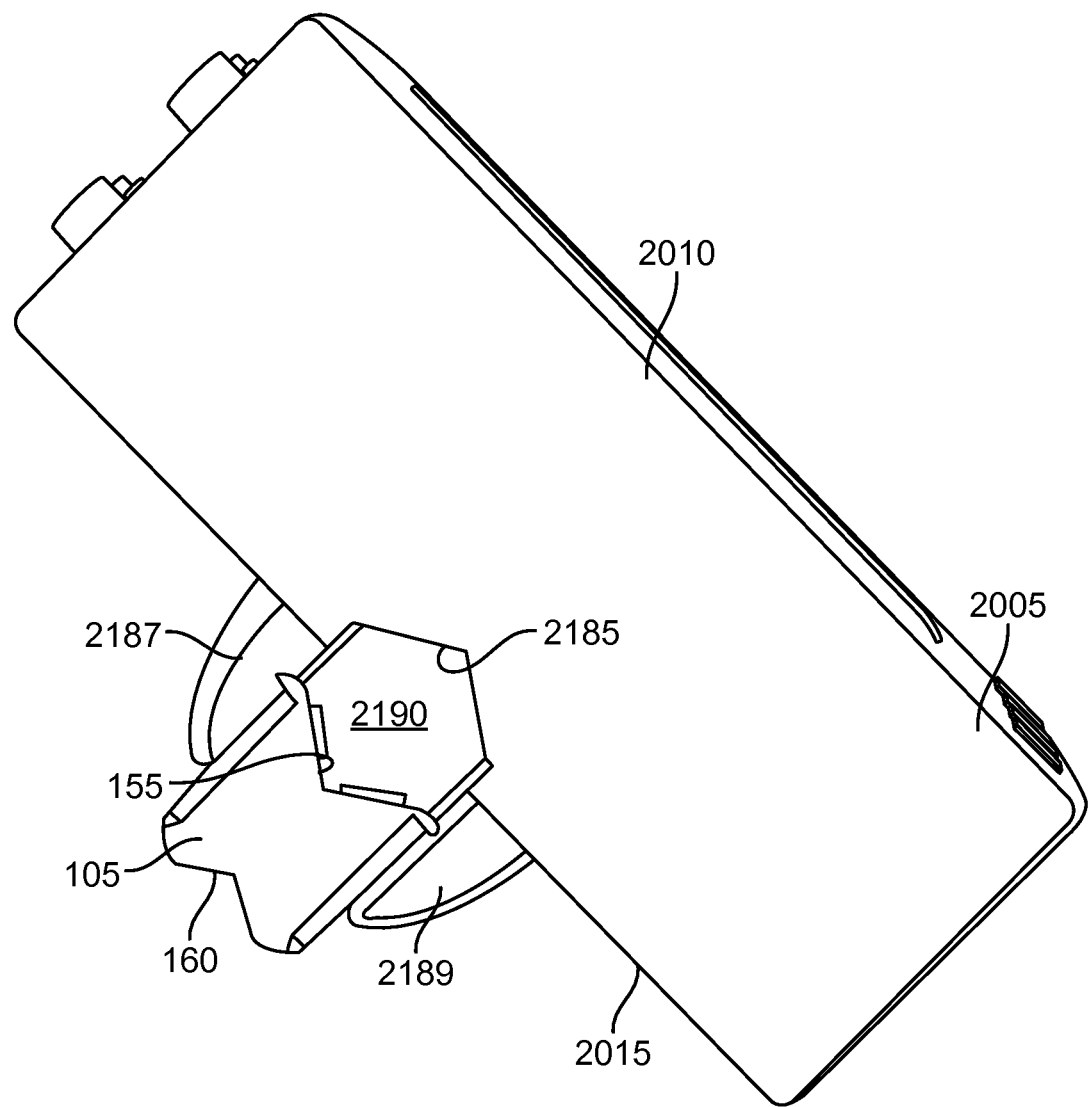
FIG. 12 is a top plan view of the equipment of FIG. 10 associated with a clamp device.

FIG. 10 shows equipment 2000 that can be mounted onto a support structure using the clamp devices described herein. The type of equipment 2000 mounted can vary and is illustrative and not intended to be limiting. In some implementations, the equipment 2000 can be a patient monitoring device having a housing 2005. A first side 2010 of the housing 2005, such as the front side, can include, for example, a screen or user interface. In some implementations, as shown in FIG. 11, a second side 2015 of the equipment 2000, such as the back side, can incorporate a slider feature 2110. It should be appreciated that another region such as a side, top, or bottom region of the housing 2005 can have an integrated slider feature 2110. In such implementations, the clamp device can include only the base 105 and the slider can be integrated with the housing 2005 of the equipment 2000 being mounted by the clamp device. The slider feature 2110 integrated with the housing 2005 can include a first arm 2187 projecting outward from a region of the second side 2015 of the housing 2005 and a second arm 2189 located a distance away from the first arm 2187 and projecting outward from a second region of the second side 2015 of the housing 2005 parallel to the first arm 2187. A channel 2185 can extend between the first arm 2187 and the second arm 2189 that is sized to receive at least a portion of an elongate support structure 2200. In some implementations, the channel 2185 can be recessed within the second side 2015 of the housing 2005 (see FIG. 12). The base 105 can slide through this channel 2185 such that the arms 2187, 2189 extend over at least a portion of the sides 130, 135 of the base 105 when the equipment 2000 is engaged with the base 105.

The inner surfaces of the arms 2187, 2189 can each have coupling elements configured to engage corresponding coupling elements of the base 105, such as a groove 2165 configured to engage a track 150 as described elsewhere herein. The inner surface of the first arm 2187 facing towards the second arm 2189 and the inner surface of the second arm 2189 facing towards the first arm 2187 can each include a coupling element configured to engage with a corresponding coupling element of the base 105 received therebetween. Inner surfaces of the arms 2187, 2189 can engage with the base 105 such as via a tongue and groove arrangement capturing the support structure 2200 therebetween.

Each groove 2165 can extend at an angle, for example, an angle away from the front side 2010 of the equipment 2000 such that a first end region of each groove 2165 can be located a first distance from the front side 2010 of the equipment 2000 and a second end region of each groove 2165 can be located a second distance from the front side 2010 of the equipment 2000. The angle can also be described as an angle away from a plane parallel with a user viewing side of the equipment 2000 such that the first end region of each groove 2165 is located a first distance from the plane and the second end region of each groove 2165 can be located a second distance from the plane. The pair of angled grooves 2165 are configured to receive and engage with angle tracks 150 of the base 105 upon engaging the equipment 2000 onto the base 105. Thus, the angle of the grooves 2165 generally matches the angle of the tracks 150.

Figure 13:
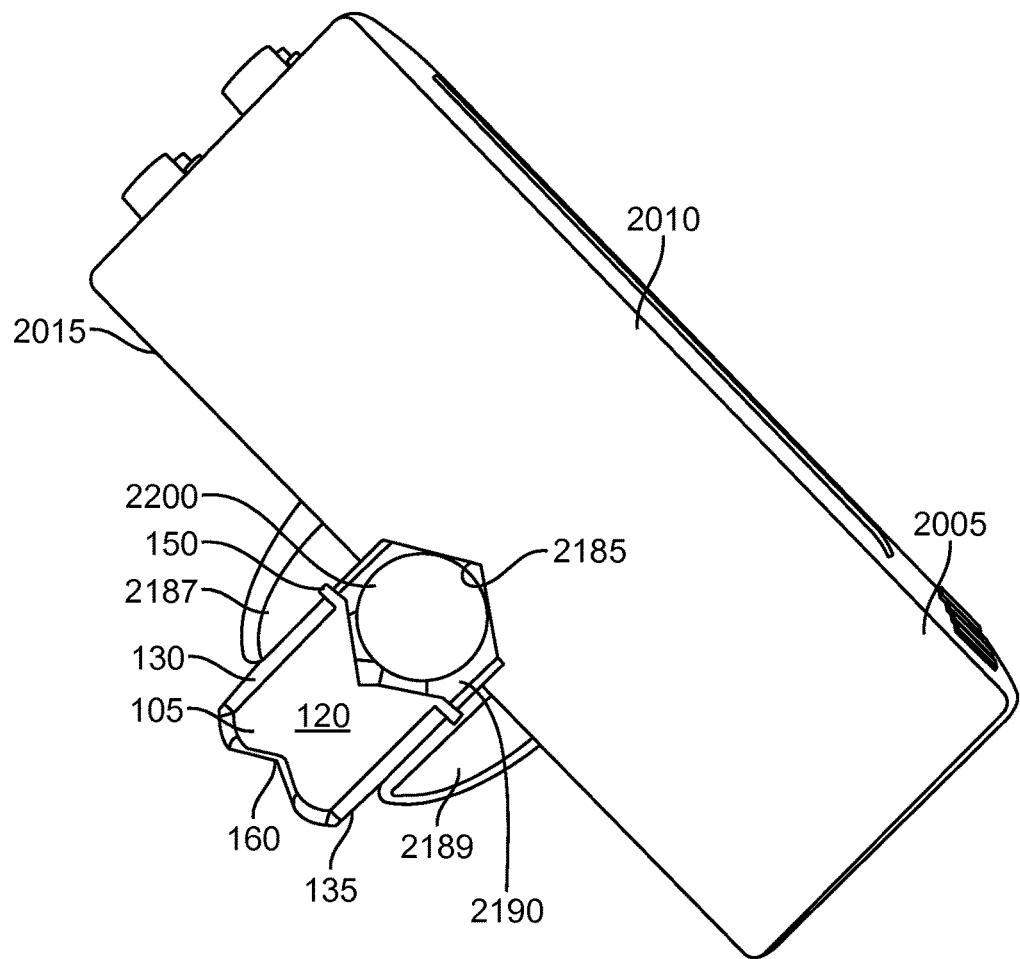
FIG. 13 is a top plan view of the equipment of FIG. 10 mounted on a support structure using the clamp device.

As described herein the base 105 can include at least one trough 155. An inner region of the channel 2185 can face the trough 155 of the base 105 and collectively form a space 2190 between the base 105 and the equipment 2000 within which the support structure 2200 can extend (see FIG. 12). The slider feature 2110 of the equipment 2000 can engage with the base 105 from the top end 120 down such that the support structure 2200 is captured within the space 2190 collectively formed between the trough 155 of the base 105 and the channel 2185 of the slider feature 2110 of the equipment 2000 (see FIG. 13). As the equipment 2000 slides relative to the base 105 from the top end 120 towards the bottom end 125 and the grooves 2165 receive the tracks 150 of the base 105, the association between the equipment 2000 and the base 105 becomes tighter and the space 2190 narrows. The narrowing of the space 2190 forms a compressive grip on the support structure 2200 positioned within the space 2190. The equipment 2000 can be moved to contact or be positioned onto a second side of the support structure 2200 such that the support structure 2200 is captured between the base 105 and the equipment 2000 although it should be appreciated that during use, both the equipment 2000 and the base 105 can be moveable relative to one another. Generally, the base 105 can be positioned onto a first side of the support structure 2200 and the equipment 2000 moved downward onto the base 105. The relative position of both the base 105 and the equipment 2000 to the support structure 2200 can be optimized prior to the final clamping of the equipment 2000 onto the base 105. The clamping effect can be assisted by gravity and the weight of the equipment 2000 mounted by urging the equipment further downward relative to the base 105.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together."

Use of the term "based on," above and in the claims is intended to mean, "based at least in part on," such that an unrecited feature or element is also permissible.

What is claimed is:

1. A clamp device for mounting equipment to a support structure, the clamp device comprising:
    a base having opposing front and back sides, opposing top and bottom ends, and opposing first and second lateral sides, the base comprising:
    a first trough formed in the front side of the base and a second trough formed in the back side of the base, the first trough and the second trough being V-shaped; and
    a first coupling element located on the first lateral side and a second coupling element located on the second lateral side of the base,
    wherein each of the first and second coupling elements extend from near the top end of the base towards the bottom end of the base at an angle relative to the first trough; and
    a slider comprising a channel on a back side of the slider and corresponding coupling elements within the channel configured to slidingly engage the first and second coupling elements of the base upon association of the slider with the base.

2. The clamp device of claim 1, wherein the slider reversibly and alternatingly associates with the base such that the corresponding coupling elements within the channel slidingly engage the first and second coupling elements of the base in a first coupled configuration by sliding downwards from the top end of the base towards the bottom end of the base when the first trough faces the channel and in a second coupled configuration by sliding downwards from the bottom end of the base towards the top end of the base when the second trough faces the channel.

3. The clamp device of claim 2, wherein the first trough and the channel when in the first coupled configuration and the second trough and the channel when in the second coupled configuration collectively form a space between the base and the slider that narrows as the slider moves downwards relative to the base.

4. The clamp device of claim 3, wherein the space is sized to accommodate a support structure.

5. The clamp device of claim 4, wherein the support structure has an outer diameter in a range of about 0.5 inches to about 1.25 inches.

6. The clamp device of claim 4, wherein the slider urges the support structure against the first trough in the first coupled configuration as the slider moves downwards towards the bottom end of the base and the space is narrowed, and wherein the slider urges the support structure against the second trough in the second coupled configuration as the slider moves downwards towards the top end of the base and the space is narrowed.

7. The clamp device of claim 1, wherein the first trough has a shape configured to accommodate a support structure having a first outer diameter and the second trough has a shape configured to accommodate a support structure having a second outer diameter, wherein the first outer diameter is larger than the second outer diameter.

8. The clamp device of claim 4, wherein the base contacts a first side of the support structure and the slider contacts a second side of the support structure upon association of the slider with the base.

9. The clamp device of claim 1, further comprising one or more compliant elements coupled to one or more regions of the base.

10. The clamp device of claim 9, wherein the one or more compliant elements include an elastomeric over-mold coupled within the first and second troughs.

11. The clamp device of claim 1, further comprising a tether having a first end coupled to a region of the base and a second end coupled to a region of the slider.

12. The clamp device of claim 1, wherein the coupling elements of the base are a pair of tracks and the corresponding coupling elements within the channel of the slider are a pair of grooves.

13. The clamp device of claim 1, wherein the corresponding coupling elements within the channel extend at an angle that is the same as the angle at which the first and second coupling elements extend relative to the first trough.

14. The clamp device of claim 1, wherein the angle is between about 10 degrees and about 15 degrees.

15. The clamp device of claim 1, wherein the slider comprises a mounting feature on a front side of the slider.

16. The clamp device of claim 1, wherein the base has a longitudinal axis extending between the top and bottom ends, and wherein the first and second troughs extend parallel to one another and parallel to the longitudinal axis.

17. The clamp device of claim 1, wherein the first trough formed in the front side of the base and the second trough formed in the back side of the base each extend from the top end of the base to the bottom end of the base.

18. A mounting clamp system comprising:
    a base comprising:
    opposing front and back sides, opposing top and bottom ends, and opposing first and second lateral sides;
    a first trough formed in the front side of the base and a second trough formed in the back side of the base; and
    a first coupling element located on the first lateral side and a second coupling element located on the second lateral side of the base,
    wherein each of the first and second coupling elements extends from near the top end of the base towards the bottom end of the base at an angle relative to the first trough;
    and equipment comprising a slider feature integrated with a housing of the equipment,
    the slider feature comprising:

a first arm projecting outward from a first region of the housing and having an inner surface;

a second arm located a distance away from the first arm and projecting outward from a second region of the housing parallel to the first arm, the second arm having an inner surface facing the inner surface of the first arm;

a channel located between the first arm and the second arm sized to receive at least a portion of an elongate support structure; and a third coupling element located on the inner surface of the first arm and a fourth coupling element located on the inner surface of the second arm, wherein each of the third and fourth coupling elements extend from near a top end of the first and second arms towards a bottom end of the first and second arms such that the third coupling element slidingly engages the first coupling element and the fourth coupling element slidingly engages the second coupling element upon association of the slider feature with the base.

19. The clamp device of claim 1, wherein the coupling elements of the base are grooves and the corresponding coupling elements within the channel of the slider are tracks.

20. A clamp device for mounting equipment to a support structure, the clamp device comprising:

a base having opposing front and back sides, opposing top and bottom ends, and opposing first and second lateral sides, the base comprising:

a first trough formed in the front side of the base and a second trough formed in the back side of the base, the first trough and the second trough each extending from the top end of the base to the bottom end of the base; and a first coupling element located on the first lateral side and a second coupling element located on the second lateral side of the base, wherein each of the first and second coupling elements extend from near the top end of the base towards the bottom end of the base at an angle relative to the first trough; and a slider comprising a channel on a back side of the slider and corresponding coupling elements within the channel configured to slidingly engage the first and second coupling elements of the base upon association of the slider with the base.

21. The clamp device of claim 20, wherein the slider reversibly and alternatingly associates with the base such that the corresponding coupling elements within the channel slidingly engage the first and second coupling elements of the base in a first coupled configuration by sliding downwards from the top end of the base towards the bottom end of the base when the first trough faces the channel and in a second coupled configuration by sliding downwards from the bottom end of the base towards the top end of the base when the second trough faces the channel.

22. The clamp device of claim 21, wherein the first trough and the channel when in the first coupled configuration and the second trough and the channel when in the second coupled configuration collectively form a space between the base and the slider that narrows as the slider moves downwards relative to the base.

23. The clamp device of claim 22, wherein the space is sized to accommodate a support structure.

24. The clamp device of claim 23, wherein the support structure has an outer diameter in a range of about 0.5 inches to about 1.25 inches.

25. The clamp device of claim 23, wherein the slider urges the support structure against the first trough in the first coupled configuration as the slider moves downwards towards the bottom end of the base and the space is narrowed, and wherein the slider urges the support structure against the second trough in the second coupled configuration as the slider moves downwards towards the top end of the base and the space is narrowed.

26. The clamp device of claim 23, wherein the base contacts a first side of the support structure and the slider contacts a second side of the support structure upon association of the slider with the base.

27. The clamp device of claim 20, wherein the first trough has a shape configured to accommodate a support structure having a first outer diameter and the second trough has a shape configured to accommodate a support structure having a second outer diameter, wherein the first outer diameter is larger than the second outer diameter.

28. The clamp device of claim 20, wherein the first trough and the second trough are V-shaped.

29. The clamp device of claim 20, further comprising one or more compliant elements coupled to one or more regions of the base.

30. The clamp device of claim 29, wherein the one or more compliant elements include an elastomeric over-mold coupled within the first and second troughs.

31. The clamp device of claim 20, wherein the coupling elements of the base are a pair of tracks and the corresponding coupling elements within the channel of the slider are a pair of grooves.

32. The clamp device of claim 20, wherein the corresponding coupling elements within the channel extend at an angle that is the same as the angle at which the first and second coupling elements extend relative to the first trough.

33. The clamp device of claim 20, wherein the angle is between about 10 degrees and about 15 degrees.

34. The clamp device of claim 20, wherein the slider comprises a mounting feature on a front side of the slider.

35. The clamp device of claim 20, wherein the base has a longitudinal axis extending between the top and bottom ends, and wherein the first and second troughs extend parallel to one another and parallel to the longitudinal axis.

36. The clamp device of claim 20, wherein the coupling elements of the base are grooves and the corresponding coupling elements within the channel of the slider are tracks.

* * * * *